United States Patent [19]

Prisbylla

[11] Patent Number: 5,278,133
[45] Date of Patent: Jan. 11, 1994

[54] PYRIDONE HERBICIDES

[75] Inventor: Michael P. Prisbylla, Richmond, Calif.

[73] Assignee: Imperial Chemical Industries plc, London, Great Britain

[21] Appl. No.: 989,308

[22] Filed: Dec. 11, 1992

[51] Int. Cl.$^5$ ............... C07D 213/20; C07D 213/54; A01N 43/40
[52] U.S. Cl. ........................ 504/130; 546/288; 546/290; 546/303
[58] Field of Search ............ 514/344, 380; 546/288, 546/290, 303; 504/130

[56] References Cited

U.S. PATENT DOCUMENTS 3,634,435  1/1972  Trueb et al. ................. 546/303

OTHER PUBLICATIONS

Taylor, et al., Tetrahedron 43, 5145 (1987).
Taylor, et al., Bull Soc. Shim. Belg. 97, 599 (1988).

*Primary Examiner*—C. Warren Ivy
*Assistant Examiner*—D. Margaret M. Mach
*Attorney, Agent, or Firm*—Joel G. Ackerman

[57] ABSTRACT

Compounds having the formula in which:
R is hydrogen, 2-halo, 2-($C_1$–$C_4$ alkyl), 2-trifluoromethyl, 2-($C_1$–$C_4$ alkoxy), 4-fluoro or, 2,6-dihalo;
$R_1$ is halo, cyano, $C_1$–$C_4$ alkyl, or trifluoromethyl, and if R is 2-halo, 2-methyl, 2-methoxy or 2,6-dihalo, then $R_1$ may also be hydrogen; and
$R_2$ is halo, are herbicides.

10 Claims, No Drawings

PYRIDONE HERBICIDES

FIELD OF THE INVENTION

This invention relates to certain pyridone compounds which demonstrate herbicidal activity.

DESCRIPTION OF THE INVENTION

According to this invention, compounds of the following structure have been found to exhibit herbicidal activity:

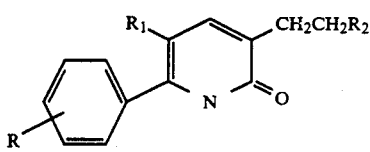

in which:
R is hydrogen, 2-halo, 2-($C_1$–$C_4$ alkyl), 2-trifluoromethyl, 2-($C_1$–$C_4$ alkoxy), 4-fluoro or, 2,6-dihalo;
$R_1$ is halo, cyano, $C_1$–$C_4$ alkyl, or trifluoromethyl, and if R is 2-halo, 2-methyl, 2-methoxy or 2,6-dihalo, then $R_1$ may also be hydrogen; and
$R_2$ is halo.

"Alkyl" includes both straight and branched chain groups having the indicated number of carbon atoms. "Halo" includes chloro, fluoro, bromo and iodo.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", it is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, primarily as pre-emergent herbicides, namely herbicides which are applied prior to emergence of vegetation from the soil. Some of the compounds of this invention demonstrate good to excellent control of nutsedge, a particularly difficult type of weed to control.

Compounds of this invention may be prepared by opening the ring of a corresponding substituted 2,3-dihydrofuro[2,3-b]pyridine compound with a concentrated hydrohalide such as hydrochloric or hydrobromic acid, with heating, according to the reaction:

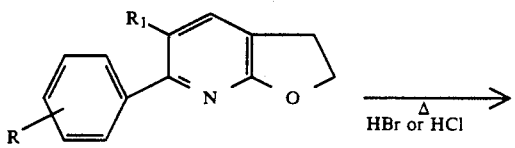

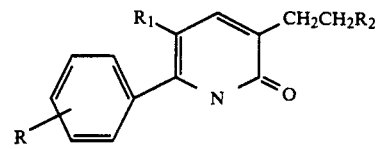

The fused pyridine compounds in which $R_1$ is hydrogen, $C_1$–$C_4$ alkyl, or trifluoromethyl are prepared by the following general process:

(a) a phenylglyoxal is reacted with S-methylthiosemicarbazide to produce a substituted 3-methylthio-1,2,4-triazine

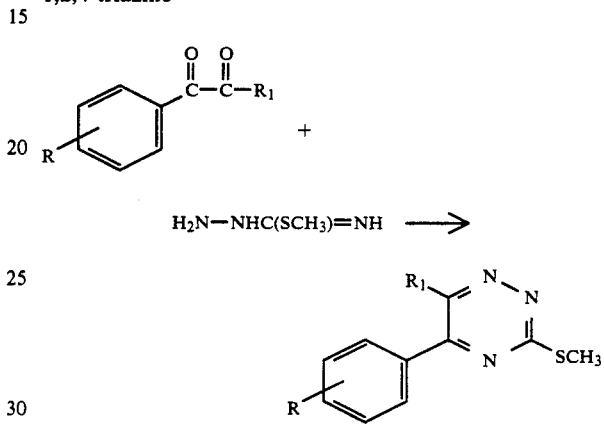

This reaction is conducted in the presence of sodium bicarbonate in 50/50 (v/v) aqueous ethanol or in dioxane, at room temperature.

(b) The methylthiotriazine of step (a) is oxidized conventionally to the corresponding sulfone.

(c) The sulfone is displaced with an anion prepared from 3-butyn-1-ol in the presence of a base such as sodium hydride in tetrahydrofuran or another conventional

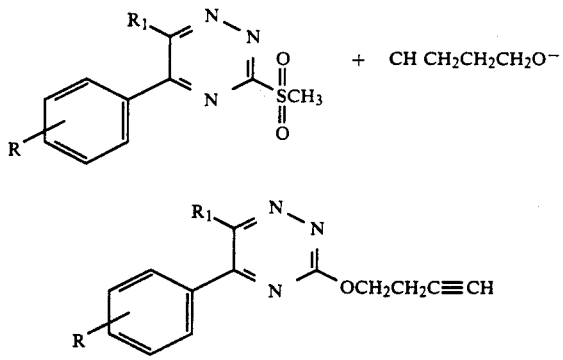

(d) The butynyloxy-substituted triazine is cyclized by heating to reflux in an inert solvent, preferably a halobenzene solvent:

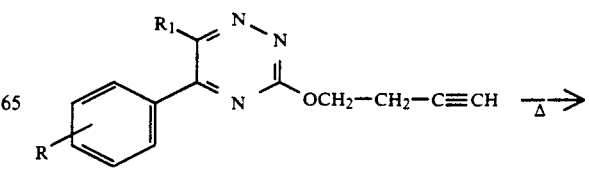

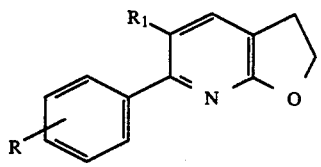

Processes of this type are discussed in Taylor, et al., Tetrahedron 43, 5145 (1987) and Taylor, Bull. Soc. Chim. Belg. 97, 599 (1988) and in my copending application, filed on even date herewith and commonly assigned, entitled "Fused Pyridine Herbicides" (attorney docket, PR-8643).

Compounds of this invention in which $R_1$ is a halogen are obtained by halogenation of the product of step (d) with a halogenating agent such as elemental halogen, trichloroisocyanuric acid, etc. under conventional conditions.

The following represents an example of the preparation of a compound of this invention.

Preparation of 6-phenyl 5-bromo-3-(2-bromoethyl) pyridiine-2-one (Compound 3 herein)

(a) Phenylglyoxal (11.1 g, 0.073 mmol) was dissolved in 70 ml dioxane. Then there was added 70 g crushed ice followed by 22.5 g (0.096 mmol) S-methylthiosemicarbazide iodide, and 9.1 g (0.108 mmol) sodium bicarbonate. The mixture was let stand overnight then checked for completion of reaction by thin layer chromotography. When the reaction was complete the mixture was poured into ethyl acetate. The aqueous layer was extracted with ethyl acetate, and the combined extracts washed with water, dried and filtered. The filtrate was mixed with anhydrous ethanol for about two hours then washed with alcohol and dried. There was obtained 12.1 g of product; m.p. 91°–97° C.

(b) Product of Step (a) and of a second run of that reaction (total 25.4 g, 0.125 mmol) was dissolved in 650 ml methylene chloride and cooled in an ice/salt bath. There was then added 59.3 g (0.275 mmol) of 80% purity m-chloropropoxybenzoic acid (in three portions, over one hour). The temperature was maintained at −5° to 0° C. The mixture was let stand overnight while being warmed to room temperature.

The product was filtered and the filtrate was washed with sodium thiosulfate, potassium carbonate, water and brine, dried and filtered. The filtrate was stripped, producing 28.1 g of the sulfone; m.p. 180°–190° C.

(c) In a flask were combined 160 ml tetrahydrofuran and 1.95 g (65 mmol) of sodium hydride (80% dispersion in white oil). The flask was cooled and 4.55 g (65 mmol) 3-butynyl-1-ol in 40 ml tetrahydrofuran was added dropwise. The reaction mixture was allowed to warm to ambient temperature, then cooled again and 11.8 g (50 mmol) product of step b) was added. The mixture was allowed to warm and after one hour was diluted with ethyl acetate and washed with water, then dried and filtered. There was obtained 8.7 g of the desired butynyloxy compound.

(d) The product of step c) (8.2 g, 36.4 mmol) was mixed with 70 ml bromobenzene and the mixture heated to reflux. The solvent was stripped off and the residue purified by column chromatography. There was obtained 5.6 g of the desired product, 6-phenyl-2,3-dihydrofuro[2,3-b]pyridine, m.p. 83.5°–85.5° C.

(e) In a flask there was dissolved 3.0 g (15.2 mmol) of the product of step d) in 50 ml methanol. Then there was added 3.2 g (38 mmol) sodium bicarbonate, followed by 2.55 g (0.82 ml, 15.90 mmol) bromine in 15 ml methanol, dropwise. The mixture was stirred at ambient temperature overnight and the following morning some additional bromine was added. The reaction mixture was diluted with saturated sodium bicarbonate and extracted with methylene chloride. The extracts were washed with water and brine, dried and filtered, and solvent-stripped producing 4.02 g (15.2 mmol) of desired product, a viscous liquid.

(f) 6-phenyl-5-bromo-2,3-dihydrofuro[2,3-b]pyridine (1.50 gm, 5.43 mmol) was dissolved in 1,2-dichloroethane (25 ml). Aqueous HBr (48%, 25 ml) was added and the solution heated to reflux until thin layer chromatography indicated complete reaction (approximately 1–2.5 h). The reaction mixture was cooled, diluted with water and extracted with ethyl acetate. The combined extracts were washed with water, brine (sat.), dried (MgSO$_4$) filtered and concentrated to give 1.91 grams of a solid. m.p. 188°–189.5° C.

Table I depicts representative compounds of this invention, prepared by a process as described above. Most compounds were obtained as oils. Structures were confirmed by spectroscopic analyses.

TABLE I

| Compound No. | R | $R_1$ | $R_2$ |
|---|---|---|---|
| 1 | 2,6-F | Br | Br |
| 2 | H | CN | Cl |
| 3 | H | Br | Br |
| 4 | H | Br | Cl |
| 5 | H | CH$_3$ | Br |
| 6 | 2-CF$_3$ | H | Br |
| 7 | 2-Br | Cl | Br |
| 8 | 2-Br | H | Br |

Herbicidal Activity Tests

Compounds of Table I were tested for herbicidal activity as follows:

The herbicidal effect was observed by comparing the extent of weed control in test flats treated with the compounds against that occurring in similar non-treated control flats. Compounds were applied at 3.57 lb/A (4 kg/ha) or otherwise as indicated to pre-emergence and post-emergence screening flats. An 80 gal/A (748.3 l/ha) spray volume was utilized. Post-emergence flats were seeded 12 days prior to treatment. Pre-emergence flats were seeded one day prior to treatment. Overhead watering of pre-emergence flats and soil surface watering of post-emergence flats, so as to avoid wetting the foliage, were carried out for the duration of the test.

Weed seeds were planted in a flat at a seed depth of 0.5 inch (1.3 cm). Soil for flats was prepared using sandy loam soil fortified with 17-17-17 fertilizer (N—P$_2$O$_5$—K$_2$O on a weight basis) and sterilized. The test weeds were as follows:

| COMMON NAME | SCIENTIFIC NAME |
|---|---|
| green foxtail | Setaria viridis |
| watergrass | Echinochloa crus-galli |

-continued

| COMMON NAME | SCIENTIFIC NAME |
| --- | --- |
| wild oat | *Avena fatua* |
| annual morning glory | *Ipomoea purpurea* |
| velvetleaf | *Abutilon theophrasti* |
| wild mustard | *Sinapsis arvensis* |
| yellow nutsedge | *Cyperus esculentus* |

The spray solutions were prepared by dissolving 240 mg of test compound in 20 ml of acetone containing 1% polyoxyethylene sorbitan monolaurate emulsifier, then adding 20 ml of water to the resulting solution. The stock solutions were applied using a linear spray table. Pre-emergence flats are raised to the level of the post-emergence foliage canopy by setting the flats on a wooden block.

The degree of weed control was visually assessed and recorded as percentage control compared to the growth of the same species in an untreated check flat of the same age. The rating scale ranges from 0 to 100%, where 0 equals no effect with plant growth equal to the untreated control, and 100 equals complete kill. Ratings were taken approximately 15-18 days after treatment (DAT).

Results are listed in Table II below, expressed as average control of the three grasses (GR) (wild oat, water-grass, foxtail) and three broadleaf weeds (BL) (morningglory, mustard, velvetleaf), and of nutsedge (NS).

TABLE II

| | % Control, 3.57 kg/ha | | | | | |
| --- | --- | --- | --- | --- | --- | --- |
| | Pre-emergence | | | Post-emergence | | |
| Compound No. | GR avg. | BL avg. | NS | GR avg. | BL avg. | NS |
| 1 | 80 | 45 | 100 | 5 | 15 | 20 |
| 2 | 33 | 0 | 0 | 0 | 0 | 0 |
| 3 | 96 | 40 | 5 | 11 | 18 | 85 |
| 4 | 86 | 35 | 90 | 0 | 3 | 30 |
| 5 | 99 | 53 | 70 | 20 | 36 | 50 |
| 6 | 65 | 3 | 75 | 0 | 6 | 30 |
| 7 | 71 | 41 | 40 | 8 | 25 | 50 |
| 8 | 75 | 25 | 70 | 31 | 26 | 50 |

In practice, a pure compound can be used as an herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrenebutadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| EXAMPLES OF TYPICAL COMPOSITIONS | | | |
|---|---|---|---|
| Ingredient | Weight % | | |
| Oil | | | |
| Active Compound | 1 | | |
| Oil solvent-heavy aromatic naphtha | 99 | | |
| Total | 100 | | |
| Emulsifiable Concentrate | | | |
| Active Compound | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Active Compound | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application. Examples of useful complementary herbicides include:

A. Benzo-2,1,3-thiodiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;
X. amino acid herbicides such as glyphosate and gluyfosinate and their salts and esters, sulphosate, and bilanafos;
Y. organoarsenical herbicides such as MSMA;
Z. herbicidal amide derivative such as napropamide, propyzamide, carbetamide, tebutam, bromobutide, isoxaben, naproanilide, diphenamid, and naptalam;
AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;
BB. examples of useful contact herbicides include bipyridylium herbicides such as those in which the active entity is paraquat and those in which the active entity is diquat.

*These compounds are preferably employed in combination with a safener such as 2,2-dichloro-N,N-di-2-propenylacetamide (dichlormid).

What is claimed is:

1. A compound having the formula

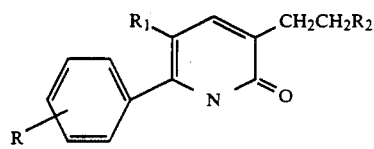

in which:
R is 2-halo, 2-($C_1$–$C_4$ alkyl), 2-trifluoromethyl, 2-($C_1$–$C_4$ alkoxy), 4-fluoro or, 2,6-dihalo;
$R_1$ is halo, cyano, $C_1$–$C_4$ alkyl, or trifluoromethyl, and if R is 2-halo, 2-methyl, 2-methoxy or 2,6-dihalo, then $R_1$ may also be hydrogen; and
$R_2$ is halo.

2. A compound according to claim 1 in which R is hydrogen, 2-halo, 2-trifluoromethyl, or 2,6-difluoro.

3. A compound according to claim 2 in which $R_1$ is bromo, chloro, methyl or trifluoromethyl.

4. A compound according to claim 1 in which R is hydrogen.

5. A compound according to claim 4 in which $R_1$ is bromo.

6. A compound according to claim 4 in which $R_1$ is methyl.

7. A compound according to claim 1 in which R is 2-bromo.

8. A compound according to claim 1 in which R is 2,6-difluoro.

9. A method of controlling undesirable vegetation comprising applying to said vegetation or the locus thereof a herbicidally effective amount of a compound having the formula

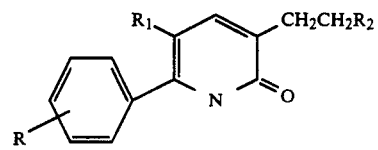

in which:
R is hydrogen, 2-halo, 2-($C_1$–$C_4$ alkyl), 2-trifluoromethyl, 2-($C_1$–$C_4$ alkoxy), 4-fluoro or, 2,6-dihalo;
$R_1$ is halo, cyano, $C_1$–$C_4$ alkyl, or trifluoromethyl, and if R is 2-halo, 2-methyl, 2-methoxy or 2,6-dihalo, then $R_1$ may also be hydrogen; and
$R_2$ is halo.

10. A herbicidal composition comprising:
a) A herbicidally effective amount of a compound having the formula

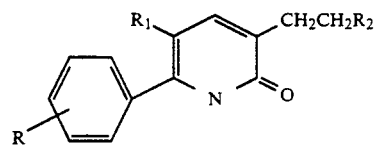

in which:
R is hydrogen, 2-halo, 2-($C_1$–$C_4$ alkyl), 2-trifluoromethyl, 2-($C_1$–$C_4$ alkoxy), 4-fluoro or, 2,6-dihalo;
$R_1$ is halo, cyano, $C_1$–$C_4$ alkyl, or trifluoromethyl, and if R is 2-halo, 2-methyl, 2-methoxy or 2,6-dihalo, then $R_1$ may also be hydrogen; and
$R_2$ is halo; and
b) a diluent or carrier suitable for use with herbicides.

* * * * *